United States Patent [19]

Wortzman

[11] Patent Number: 4,820,508
[45] Date of Patent: Apr. 11, 1989

[54] SKIN PROTECTIVE COMPOSITION

[75] Inventor: Mitchell S. Wortzman, Los Angeles, Calif.

[73] Assignee: Neutrogena Corporation, Los Angeles, Calif.

[21] Appl. No.: 65,348

[22] Filed: Jun. 23, 1987

[51] Int. Cl.⁴ .......................... A61K 7/40; A61K 7/42; A61K 7/44

[52] U.S. Cl. ......................................... 424/59; 424/60; 514/844; 514/937; 514/938

[58] Field of Search ..................................... 424/60, 59

[56] References Cited

U.S. PATENT DOCUMENTS

| | | | |
|---|---|---|---|
| 4,119,712 | 10/1978 | Goldner et al. | 424/63 |
| 4,486,405 | 12/1984 | Klein | 424/60 |
| 4,671,955 | 6/1987 | Palinczar | 424/60 |
| 4,699,779 | 10/1987 | Palinczar | 424/60 |

OTHER PUBLICATIONS

Berg, Chem. Abs., 1974, vol. 80, p. 122519y.
Derwent Abstract of Japanese Patent #49000450-A accession No. 74-66798V/38 Jan. 5, 1974, Polachem.
Horino et al, Chem. Abs., 1975, vol. 83, p. 168338d.

*Primary Examiner*—Dale Ore
*Attorney, Agent, or Firm*—Richard R. Mybeck

[57] ABSTRACT

A skin protective composition for topical application to mammalian skin for protection from infrared radiation containing titanium dioxide and mica or coated mica as its principal active reagents.

4 Claims, No Drawings

SKIN PROTECTIVE COMPOSITION

INTRODUCTION

The present invention relates generally to a skin protective composition and more particularly to a new and improved composition containing a blend of mica and titanium dioxide in a pharmacologically and cosmetically acceptable carrier and which when applied topically to exposed human skin is surprisingly effective not only in screening ultraviolet radiation but in blocking and dispersing infrared radiation from the sun and thereby substantially reducing the skin damage which otherwise would result from exposure to such solar radiation.

BACKGROUND OF THE INVENTION

While the need to protect human skin from ultraviolet radiation has been well documented during the past two decades, infrared radiation has received much less attention with respect to its cutaneous effects. Infrared photons (appreciated by the average human as a sensation of heat) are of relatively low energy. Hence, it has been stated that the inability to start photochemical reactions mitigates infrared's possible contributions to cutaneous carcinogenesis. Only recently has it been suggested that this old view might be fallacious since biochemical reactions are heat-dependent;

$-DG° = RT$ in K (where DG is the standard free energy, R is the gas constant and K is the equilibrium constant).

It is now believed that the infrared/heat axis may contribute to aging and carcinogenesis by amplifying ultraviolet injury, altering the vasculature, producing diffusible mediators, changing histone binding properties, and/or damaging DNA repair processes. (See: Kaidbey, et al, *Arch. Dermatol.*, 1982; 118 (5): 315–318.)

Present sunscreens protect against ultraviolet UVB and UVA. Unfortunately, they are no more effective than most types of glass at absorbing radiation. (see: O'Brien, J. P., *Austral J. Dermatol.*, 1980; 21: 1–9.) Infrared rays penetrate deeper than UV rays, and, once absorbed, propagate heat further by conduction and convection. (See: O'Brien, J. P., *Arch. Dermatol.*, 1975; 111: 460–466.) Therefore, present sunscreens leave the skin naked to the atmospherically transmitted infrared radiation. Absorbance and reflectance data have been generated for human skin both white and black, over the 0.4 to 1.6 m (micron) range. The reflectance curves above 1.2 m for differently pigmented persons are practically identical and reflect primarily the absorption spectrum of water. In the spectral range <0.4 m, the reflectance is usually between 50%–70% (the absorbance decreasing as the reflectance increases, indicating relative translucency). Between 0.7 and 2.6 m, water causes prominent absorption bands. This results in reflectance of only 10% from 1.4 m out to 2.6 m. These values are pertinent, especially in high atmospheric transmission wavelengths. (See: Jaquez, J. A. et al., *J. Appl. Physiol.*, 1955; 8: 297–299; and Kuppenheim, H. F. et al., *J. Appl. Physiol.*, 1955; 9: 75–78.)

Principal consideration for selecting effective sunscreens include burning, tanning, and chronic charges such as, cancer, elastosis, wrinkling, telangiectasias and pigmentary mottling. When considering the need for infrared protection, however, little information is available.

Some conditions exist which appear to be associated "purely" with heat or infrared radiation, such as, cutis laxa, that is, wizened skin of certain glass blowers, kitchen workers, bakers working with space heating devices (whose biopsies show elastosis); "Glass makers" cataract; Kang cancer of northern China (induced by sleeping or hot bricks); Kangri cancer of India (induced by wearing coal burning pots); Kairo cancer of Japan (from wearing benzene burning flasks); Peak fire cancer of Irish women; and basal cell tumors of cheeks induced by the solar focusing of rimless glasses.

Other diseases associated with infrared exposure include temporal arteritis and acitinic granuloma. (See: O'Brien, op cit; and Shabrad, P. et al., *Br. J. Dermatol.*, 1977; 97: 179–186.) in many of these entities, the cutaneous malignancies were found among the clinical changes of erythema ab igne. According to Kligman "whether heat reaches the skin by conduction (i.e., hot bricks, heating pads) or by radiation (i.e., open fires, space heaters), the changes are quite similar. Cancers and erythema ab igne can be produced by either route. (See: "Reflections on Heat", *Br. J. Dermatol*, 1984, 119: 369–355.) The possibility of erythema ab igne being a marker for infrared damage and a predictor for later skin cancers is recognized.

Histologically, smilarities between chronic actinic damage and erythema ab igne from non-burning infrared include: early elastic fiber proliferation; increased dermal mast cells; telangiectasia; epidermal dysplasia and atypia; and irregular melanin distribution. Dissimilarities include greater dermal melanin or hemosiderin deposition and less end-stage degenerative elastosis found in erythema ab igne. The mild upper dermal elastosis of erythema ab igne is superficial. This elastotic material histochemically approximates hyaluronic acid. Epidermal changes of erythema ab igne include atypia amounting to preneoplastic change and basal cell vacuolization. These effects may possibly be caused by infrared radiation, since heat has been shown to cause: cellular respiratory inhibition; decreased DNA, RNA, and protein macromolecular synthesis; increased cellular membrane permeability; decreased nucleolar-cytoplasmic transport of ribosomal RNA; and $G_2$ cell cycle phase accumulations.

Actinic elastosis has been claimed "the chief component if not the basis of aging in sun exposed skin. Also, elastosis is more prominent in biopsy than is clinically apparent." Since elastosis may be unsightly (yellow, wrinkles), preventing infrared or ultraviolet induced elastosis would be a major benefit.

At present, no direct clinical studies adquately separate solar elastosis into ultraviolet versus infrared components, and their respective proportions in humans. Finlayson's work on erythema ab igne indicates only that infrared radiation can cause elastosis in humans. (See: "Erythema ab igne: A histopathological study". *J. Invest. Dermatol.*, 1966; 46: 104–108.) Kligman showed, using guinea pigs, that ultraviolet radiation, alone, produced more numerous, thicker, twisted elastic fibers. Physiologic range infrared radiation, alone, produced numerous fine, feather-like fibers. Infrared and ultraviolet radiations simultaneously produced dense mat-like fibers and increased ground substance that exceeded the sole product of either radiation alone.

The argument has been made that actinic elastosis can be minimized by the use of present ultraviolet sunscreens. An opposing opinion was presented by Pearse, who implied that ultraviolet protection does not insure against chronic sun damage. Some believe that solar elastosis is the result of damaged fibroblasts secreting defective proteins. Infrared radiation has been shown to alter some cellular proteins (enzymes). Further studies are required to determine if infrared radiation (I.R.) affects enzymes or other proteins necessary to the manufacture of elastin.

A dramatic example of solar elastosis is the effect of I.R. on the temporal arteries. A study by O'Brien (op. cit.) reported that the outermost side of temporal arteries possesses the actinic damage similar in severity to exposed skin. Theoretically, only infrared radiation should penetrate to this depth.

Perhaps a better way to separate ultraviolet and infrared effects is through study of the black patient. The black individual, in comparison with the white, is relatively ultraviolet A and B resistant. Black skin, however has greater infrared and visible radiation absorption. Kligman and Kligman believe that "much of the elastosis in blacks is due to infrared radiation alone." This should be tempered by the fact that, of all racial groups, blacks have the least (highest resistance to) elastosis.

A unique line of reasoning implicates infrared radiation as the cause of actinic granuloma. Nigerians have a 1.7% prevalence of extremely rare granuloma multiforme, the Nigerian equivalent of actinic granuloma. Allegedly, these Nigerians differ from other blacks because they are exposed to much domestic fire radiation. Therefore, fire exposure, providing infrared radiation and convection heat, is implicated as a cause of actinic granuloma, an elastolytic condition.

The study of the individual effects of infrared or ultraviolet radiation alone may have scholarly merit; but the combination of ultraviolet and infrared radiation may have the greatest effects. Again, heat has been shown to decrease DNA repair after ionizing radiation.

In a more applicable vein, ultraviolet and heat have been shown to synergistically denature human squamous buccal mucosal DNA. This work was carried out at 24° C., 32° C. (representing the temperature of indoor surface skin), and 42° C. (representing the surface skin temperature in bright sunlight at 26° North latitude). (See: Roth and London, *J. Invest. Dermatol.*, 1977; 69; 368–372; 1977). Roth et al showed a positive linear relationship between DNA denaturation and irradiation temperature.

In a classic study, Freeman and Knox (See: *Archives of Dermatology;* 1964, 89, 858–64; 1964) showed that acute, as well as chronic, combined ultraviolet and infrared exposures may have deleterious effects on mouse skin. The mouse acute-ultraviolet-burn-death rate rose with temperature. The greatest percentages of mouse cutaneous tumors resulted from ultraviolet exposure and continuous heat as opposed to all other groups to be mentioned. Heat, delivered for three hours following a daily ultraviolet dose, resulted in a greater tumor yield than heat delivered in the intermediate three hours prior to the ultraviolet treatment. All of the aforementioned tumor yields were greater than in mice given ultraviolet therapy without exogenous heat.

While more studies may be considered necessary such as, for example, the monitoring of subjects located in variable latitudes and isolation, for both ultraviolet and infrared in regard to chronic deleterious solar effects, and biopsied, assessing one variable (i.e., infrared or ultraviolet) while holding the others constant to assess relative effects, there is sufficient evidence to give reasonable men concern that infrared is the source of deleterious cutaneous effects in man and to inspire efforts toward the development of topical preparations which can provide more than a modicum of protection of the human animal, irrespective of race or pigmentation.

BRIEF SUMMARY OF THE INVENTION

The present invention is predicated upon the surprising discovery of a novel and unique composition of matter containing, inter alia mice and titanium dioxide in a typical base which may or may not be admixed with the traditional ultraviolet (UV) absorbers and which, when applied to mammalian skin, unexpectedly disperses and blocks infrared radiation directed thereat and the ultraviolet impinged thereupon thereby protecting the skin from the severe adverse effects of both.

Accordingly, a prime object of the present invention is to provide a new and improved composition containing titanium dioxide and mica which, when topically applied to human skin provides a blocking action sufficient to reduce the skin damage which would otherwise result from exposure to unblocked infrared radiation.

A further object of the present invention is to provide a new and improved topcially applied composition which is easy to apply, cosmetically acceptable, has no adverse effect on clothing worn therewith, and demonstrates an unexpected propensity to protect mamallian skin from adverse effects of infrared radiation.

Another object of the present invention is to provide a new and improved topically applied skin protective composition whih is compatible with conventional UV-A and UV-B sunscreen reagents and can be readily admixed therewith to provide a novel multifaceted product for protection from solar radiation in the wavelength from 230–2600 nanometers.

Still another object of the present invention is to provide methods of protecting the skin of human and like susceptible animals from the adverse effects of exposure to solar radiation.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

The present invention is directed to a skin protective composition for topical application to the skin of humans and like susceptible animals (herein "mammals") having the unexpected ability to deter and prevent infrared radiation from causing dermal destruction and cancer. The present invention also embraces means and methods of inhibiting the action of both infrared and ultraviolet radiation upon mammalian skin by combining such compositions with known UV-A and UV-B blockers and applying the resulting composition to such skin.

A key factor of the present invention involves the use of titanium dioxide, heretofore recognized as effective only within ulraviolet and visible light ranges, that is, between 290–700 nanometers (See: *Federal Register,* Aug. 25, 1978, p. 38250) when it is admixed with or disposed upon particulate mice or both in a skin protective composition which has the surprising propensity to block and disperse infrared radiation, that is, radiation having a wave length of between 700–2600 nanometers.

Mica, as used herein, refers to any member of a group of mineral hydrous disilicates of aluminum with other bases, chiefly potassium, magnesium, iron and lithium that separate readily into thin, tough, often transparent and usually elastic laminae.

To provide coated mica, fine particles (circa 5-20 microns) of mica are coated with an infrared reflective amount of titanium dioxide. A suitable coated mica reagent for use herein is marketed by Rona Peral Inc. of Bayonee, N.J., a division of E. Merck, Darmstadt, Germany under the name TIMIRON ™. TIMIRON ™ Super Sheen-MP 1001 assays to 36-41% wt/wt $TiO_2$ and 64-59% mica (average values: 38.5% $TiO_2$; and 61.5% mica).

The composition of the present invention contains coated mica (with $TiO_2$) or a combination of mica and titanium dioxide as its essential ingredients disposed in pharmaceutically acceptable extending medium such as a carrier or vehicle which adapts said agents for application to the skin. Conventional ultraviolet screens or absorbers may be admixed therewith as will hereinafter appear. The compositions can be in either solid, liquid or aerosol form. The compositions of the present invention can also be incorporated into various cosmetic and personal care products such as hand and body lotions, oils, ointments, lip balm products, facial cosmetics and the like.

The amount of titanium dioxide $TiO_2$ and mica present in the compositions of the cosmetic and personal care products hereof may vary greatly but preferably will be in a range of about 1 to 10% by weight of the total composition. In a preferred practice, one or more other agents such as the conventional UV-A and UV-B absorbers, opaquers such as zinc or ferric oxide and the like, may be utilized with the $TiO_2$-mica mixture so that the concentration of the combined agents will be in the range of 4% to 30% by weight of the composition. Greater amounts of these optional agents may be incorporated into various products limited only by processing and economic considerations.

Such other agents or constituents which may be present in the compositions of the present invention include water; lanolin; vaseline; glycerol; triglycerides of fatty acids; polyethylene glycols; oxyethyleneated fatty alcohols; esters such as isopropyl palmitate; myristate and stearate; silicone oils; oleyl oleate and butyl stearate; animal, vegetable or mineral oils; fatty alcohols; glycerol monostearate, and organic and mineral waxes. These other constituents are generally used in an amount of about 10 to 97% by weight of the total formulation.

Among the cosmetic ingredients which may also be used in the composition of the present invention are: thickeners, softeners, superfatting agents, emollients, wetting agents and surface active agents, as well as preservatives, anti-foam agents, perfumes or any other compatible ingredient usually employed in cosmetics.

Among the solvents used there may be mentioned water, lower monoalcohols as well as their mixtures, or aqueous-alcoholic or oil/alcohol solutions, the alcohols preferably used being ethanol, isopropyl alcohol, propylene glycol, glycerol and sorbitol, and the aqueous-alcoholic mixtures used preferably being mixtures of water and ethyl alcohol.

The following film-forming agents and cosmetic resins are also useful in the practice of the present invention, namely: polyvinylpyrrolidone, vinylpyrrolidone/-vinyl acetate copolymers in whih the monomer ratios are from 70/30 to 30/70, vinyl acetate/unsaturated carboxylic acid copolymers such as a copolymer containing 90% of vinyl acetate and 10% of crotonic acid; terpolymers of methyl methacrylate/stearyl methacrylate/dimethylaminoethyl methacrylate; completely quaternised with dimethyl sulphate, the monomers being used particularly in the ratio 20/23/57; and a terpolymer of vinyl acetate/allyl stearate/allyloxyacetiic acid, especially in the ratio of 80/15/5; maleic anhydride/methyl vinyl ether copolymers such as those commercially referred to as "Gantrez AN" as well as the ethyl, isopropyl and butyl esters of these copolymers, and maleic anhydride/butyl vinyl ether copolymers.

Sunscreen compositions now generally available are formulated in the form of creams, lotions and oils containing as the active agents ultraviolet light absorbing chemical compounds. The active chemical compounds act to block the passage of erythematogenic radiation, by absorption, thereby preventing its penetration into the skin.

For topical application, sunscreen compositions must be non-toxic and non-irritating to the skin tissue and capable of application to the skin as a uniform continuous film. In addition, the active sunscreening agents must be chemically stable and in particular must be resistant to chemical and photodegradation when on the skin as well as resistant to absorption through the skin. Among the widely used ultraviolet absorbing sunscreening agents meeting the aforesaid conditions are: oxybenzone(2-hydroxy-4-methoxybenzophenone); dioxybenzone(2,2'-dihydroxy-4-methoxybenzophenone); amino benzoic acid; cinoxate(2-ethoxyethyl-p-methoxycinnamate); diethanolamine-p-methoxycinnamate; digalloyl trioleate ethyl 4-bis(hydroxypropyl)aminobenzoate; 2-ethylhexyl-2-cyano-3,3-diphenylacrylate; ethylhexyl-p-methoxycinnamate; 2-ethylhexyl salicylate; glyceryl aminobenzoate; homosalate(3,3,5-trimethylcyclohexyl salicylate); triethanolamine salicylate; 2-phenylbenzimidazole-5-sulfonic acid; sulisobenzone(2-hydroxy-4-methoxybenzophenone-5-sulfonic acid); Padimate A (amyl p-dimethylaminobenzoate); Padimate 0 (octyl dimethyl para aminobenzoate); 4-t-butyl-4'-methoxy-dibenzoylmethane; the combination of 2-hydroxy-1,4-naphthoquinone with dihydroxyacetone; and menthyl anthranilate.

Each of the foregoing compounds have been used alone or in combination in various sunscreen compositions and been found to provide varying sun protection factors (SPF) when evaluated in human subject utilizing standard solar simulator tests.

The sunscreen material for ultraviolet-A (320-400 nm) is selected from the group comprising the pentyl and 2-ethylhexylesters of 4-(dimethylamino) benzoic acid; dioxybenzone; ethylhexyl-p-methoxy-cinnamate; ethyl 4-bis(hydroxypropyl)aminobenzoate; 3,3,5-trimethylcyclohexyl salicylate; 2-ethylhexyl-2-cyano-3,3 diphenylacrylate; 2-ethylhexyl salicylate; 4-t-butyl-4'-methoxydibenzoylmethane and mixtures thereof. The sunscreen material is present in amounts ranging from 1.0% to 20.0%, preferably 4.0% to 11.0% by weight of the total composition.

The mica-titanium dioxide mixture to combined UV-A and UV-B filters when the filters are employed will be generally 1:1 to 1:10.

In one practice of the present invention, a suitably sized stainless steel tank is charged with mineral oil and the dual mixers (the sweep rotating at about 10 RPM clockwise while the turbine rotates at about 12 RPM counterclockwise) are activated. Next a suitable solvent-carrier such as PEG-7 Glyceryl Cocoate is added followed by an oil such as cetearyl isononanoate and an ultraviolet B absorber, such as octyl methoxycinnamate, with continued mixing.

Next, the batch is heated to 78°-80° and, while heating, stearalkonium hectorite and propylene carbonate are added and the mixing is accelerated (sweep at 14 RPM and turbine at 24 RPM) until the gel is completely and homogeneously dispersed.

With the mixers at the speed indicated, an ultraviolet A absorber, such as benzophenone-3, is introduced and completely dissolved into the batch.

Next, the mica and the titanium oxide are added to the batch while the mixers are maintained at the higher speed and the temperature is maintained at 78°-80° C. for one hour.

Added next with stirring is a suitable antioxidant such as dl-alpha-tocopherol and a suitable cosmetic additive such as cyclomethicone. When these ingredients are completely blended into the batch, fumed silica (AEROSIL®) or other suitable thickening agent is added while speeding up the mixers (sweep 14 RPM; turbine 35 RPM) and maintaining the mixing until a homogeneous paste is created.

The batch is then cooled at a rate of about 0.5° C./minute until a temperature of 25°-27° C. is reached. The batch, subject to Quality Control approval is now ready for packaging.

Using the foregoing procedure, compositions embodying the present invention werre prepared as shown below, the ingredients other than mica and titanium dioxide being shown as repesentative.

| Ingredient | wt/wt percent |
|---|---|
| Mineral Oil | 24.5–79.4 |
| $C_{12-15}$ Alcohol benzoate | 5–30 |
| Octyl methoxycinnamate | 1–7.5 |
| Fumed silica | 1–8.0 |
| Mica - Titanium dioxide coated | 0.5–5 |
| Titanium dioxide | 0.5–4 |
| Propylene/carbonate and Stearalkonium hectorite | 1–10 |
| Benzophenone-3 | 1–5 |
| Cyclomethicone | 0.5–3.0 |
| dl-alpha tocopherol | 0.1–1.0 |
| PEG-7 glycerol cocoate | 1–5 |
| Cetearyl Isononanoate | 1–5 |

As will appear hereafter, when TIMIRON ™ coated mica is employed in place of uncoated mica, the ultimate product assay must be adjusted to reflect the additional $TiO_2$ contained therein (38.5% of the coated mica is $TiO_2$ and 61.5% is "pure" mica).

The several compositions produced in accordance with the present invention were measured, using the protocol described below, to determine the amount of infrared radiation which is "blocked" by the formulation. Whether the blockage or non-transferance resulted from reflection, dispersion or absorption was considered irrelevant and therefore not determined.

One test procedure, designated "The Spectrophotometer Procedure" will now be described.

Test formulations were applied to a 24×36 mm area of 5 mil cellulose triacetate (CTA) at a concentration of 2 microliters per square centimeter (total 17.3 microliters) using a micrometer syringe. Two sections of the applied area were scanned through the wave lengths of the Terresterial infrared (IR) range (600-2600 nanometers) using a Cary 14 Double Beam Spectrophotometer. The zero point of the Spectrophotometer was set a 0.05 O.D. on the chart recorder to control any possible negative drift of the zero point. Air vs. air and CTA vs. CTA were scanned as controls and the controls were repeated after the last sample to detect drift with time.

The means of the test runs are collected by CTA control at 200 nanometer intervals and converted to percent transmission (T=Antilog-OD). The "means % T" was calculated and 100%-mean %T is interpreted as average percent IR Blocked. This was done over the 600 to 2600 nanometers and the 800 to 2600 nanometer range to cover the two most used definitions of the Terrestrial IR Range.

As used above, O.D. means "optical density"; Mean T means "means transmission" and the calculations are based on Beer's Law. The concentration of 2 microliters per square centimeter was chosen because it is the U.S. government standard for evaluating UV-B sunscreens. There is presently no government standard for evaluating infrared blocking because of the pioneering nature of the present invention.

A second test procedure, designated "The Photographic Procedure", is useful to screen formulations. It will now be described.

The sunscreen efficacy of compositions embodying the present invention and the several components thereof were estimated using I.R. sensitive film (Kodak 2481) to measure the amount of radiation transmitted through a substrate upon which the formulation to be tested is dispersed at a concentration of 2 microliters per square centimetrer.

In one series of tests, IR transparent material such as MYLAR®-D (Catalina Plastics, Burbank, CA) is used for the substrate and a Xenon lamp is used a source of infrared. The coated substrate is interposed between the source lamp and the film. A suitable diffusion filter is positioned between the lamp and the substrate and an IR Pass filter (87) and a lens are disposed seriatim between the substrate and the film.

The exposure obtained on the film is proportioned to the amount of infrared penetration through the sun screen sample. It also allows a determination of the amount of infrared which did not penetrate the coated substrate. Whether this blockage or non-transference resulted from reflection, dispersion or absorption was considered irrelevant and therefore not determined.

The photographic technique herein described is primarily used to screen formulations to determine whether the test formulation is capable of blocking any infrared radiation when applied to the carrier substrate at the indicated concentration. One drawback of the photographic technique arises from the fact that the commercially available infrared photographic film (Kodak 2481) is truly sensitive only across the near infrared range between 700 and 1000 nanometers. While these wave lengths represent the majority of terrestrial infrared radiation, it does not cover it all.

To further illustrate the present invention, and not by way of limitation, the following examples are presented.

EXAMPLE 1

The materials listed under phase A are placed in a suitably sized vessel and admixed. When these materials are blended to a uniform consistency and composition, the materials listed under Phase B are added to the extant mixture. All of the materials in the vessel are then admixed in the conventional manner. The IR blocker is then added to the mixture and blended throughout. Any additional materials are then added as necessary and blended throughout the mixture.

The mixing time, temperature, and number of phases is, of course, dictated by the particular materials used. All such mixing is done in the conventional manner and the phases are introduced in alphabetical sequence.

EXAMPLE 2

Using the method of Example 1, the following are combined by weight percent:

| Phase A | |
| --- | --- |
| Purified Water USP | 58.0 |
| Glycerine, 96% | 5.0 |
| Methyl Parahydroxybenzoate | .2 |
| DEA Methoxycinnamate | 5.0 |
| Phase B | |
| Hydrogenated Polyisobutene | 3.0 |
| 1-Hexadecanol | 2.5 |
| 1 Ocatadecanol | 2.5 |
| glyceryl stearate and PEG 100 stearate | 3.0 |
| Cholesterol USP | 1.0 |
| $R(OCH_2CH_2)_n OH$ | 5.0 |
| Where R represents a blend of cetyl and stearyl radicals and n has an average value of 20 | |
| Oxybenzone (2-hydroxy-4-methoxybenzophenone) | 3.0 |
| Dimethicone 1000 cps | 5.0 |
| 4-Hydroxybenzoic Acid, Propyl Ester | 0.01 |
| Mica | 2.0 |
| Titanium Dioxide | 2.0 |
| Phase C | |
| Purified Water USP | 3.0 |
| N',N"—Methylenebis[N'—[1-(Hydroxymethyl)-2,5-Dioxo-4-Imidazolidinyl]Urea] | 0.3 |

EXAMPLE 3

Using the method of Example 1, the following are combined, by weight percent:

| Phase A | |
| --- | --- |
| Purified Water USP | 66.5 |
| Glycerol | 4.5 |
| Methyl Parahydroxybenzoate | 0.5 |
| DEA Methoxycinnamate | 4.0 |
| Phase B | |
| Isopropyl stearate | 5.0 |
| 1-Octadecanol | 4.0 |
| glyceryl stearate and PEG 100 stearate | 5.0 |
| Oxybenzone | 4.0 |
| Lanolin | 3.0 |
| Dimethicone 1000 cps | 3.5 |
| Coated mica (TIMIRON TM) | 2.0 |
| Titanium Dioxide | 2.0 |

EXAMPLE 4

Using the method of Example 1, the following are combined, by weight percent:

| Phase A | |
| --- | --- |
| Purified Water USP | 53.0 |
| Lanolin | 5.0 |
| 4-phenyl-benzophenone | 3.5 |
| DEA Methoxycinnamate | 4.5 |
| Phase B | |
| 1-Hexadecanol | 3.5 |
| 3,3,5-trimethylcyclohexyl salicylate | 4.5 |
| p dimethyl-aminobenzoate | 4.5 |
| Oxybenzone | 3.0 |
| 4-hydroxybenzoic acid, propyl ester | 0.5 |
| Butyl stearate | 5.0 |
| Mica | 1.0 |
| Titanium Dioxide | 3.0 |
| Phase C | |
| Glycerol monostearate | 4.0 |
| Mineral oil | 5.0 |

EXAMPLE 5

Using the method of Example 1, the following are combined, by weight percent:

| Phase A | |
| --- | --- |
| Purified Water USP | 33.0 |
| Glyceryl stearate and PEG 100 stearate | 5.5 |
| Mineral oil | 7.5 |
| Glycerol monostearate | 10.0 |
| Isopropyl myristate | 8.0 |
| Ethanol | 8.0 |
| Phase B | |
| Polyvinyl pyrrolidone | 5.0 |
| Octyl-dimethyl-para-amino benzoate | 4.0 |
| p-amino-benzoic acid | 1.5 |
| Glyceryl amino benzoate | 1.0 |
| p-dimethylamino benzoate | 3.5 |
| Mica | 2.0 |
| Titanium Dioxide | 5.0 |
| Phase C | |
| Isopropyl palmitate | 3.5 |
| BHA | 2.5 |

EXAMPLE 6

Using the method of Example 1, the following are combined by weight percent:

| Phase A | |
| --- | --- |
| Purified Water USP | 82.5 |
| Ethanol | 5.0 |
| Hydroxyethyl cellulose | .50 |
| Phase B | |
| Oxybenzone | 3.0 |
| Mica | 5.0 |
| Titanium Dioxide | 2.0 |
| Phase C | |
| p dimethylamino benzoate | 2.0 |

EXAMPLE 7

In another practice of the present invention, a suitably sized stainless steel tank is charged with mineral oil and the dual mixers (the sweep rotating at about 10 RPM clockwise while the turbine rotates at about 12 RPM counterclockwise) are activated. Next a suitable solvent-carrier such as PEG-7 Glycerol Cocoate is added followed by an oil such as cetearyl isononanoate, a filler, such as silica, a solvent such as C12-15 alcohol benzoate (Finesolv), and an ultraviolet B absorber, such as octyl methoxycinnamate, with continued mixing.

Next, the batch is heated to 78°-80° and, while heating, stearalkonium hectorite and propylene carbonate (Cetiol SN) is added and the mixing is accelerated (sweep at 14 RPM and turbine at 24 RPM) until the gel is completely and homogeneously dispersed.

With the mixers at the speed indicated, an ultraviolet A absorber, such as benzophenone-3 is introduced and completely dissolved into the batch. Next, the mica and the titanium dioxide are added to the batch while the mixers are maintained at the higher speed and the temperature is maintained at 78°–80° C. for one hour.

Added next with stirring is a suitable antioxidant such as dl alpha tocopherol and a suitable cosmetic additive, such as cyclomethicone. When these ingredients are completely blended into the batch, the mixers are sped up (sweep 14 RPM; turbine 35 RPM) and maintained at the increased speed until a homogeneous paste is created.

The batch is then cooled at a rate of about 0.5° C./minute until a temperature of 25°–27° C. is reached. The batch is then ready for packaging.

Using the foregoing procedure, compositions embodying the present invention were prepared as shown below:

| Ingredient | wt/wt % |
| --- | --- |
| Mineral Oil | 25.5–88.4 |
| $C_{12-15}$ Alcohol benzoate | 5–30 |
| Octyl methoxycinnamate | 1–7.5 |
| Fumed silica | 1–8 |
| Mica | 0.5–5 |
| Titanium Dioxide | 0.5–4 |
| Propylene/carbonate and Stearalkonium hectorite | 1–10 |
| Benzophenone-3 | 1–5 |
| Cyclomethicone | 0.5–3.0 |
| dl-alpha tocopherol | 0.1–1.0 |
| PEG-7 glycerol cocoate | 1–5 |
| Cetearyl Isononanoate | 1–5 |

EXAMPLE 8

Using the procedure of Example 7, an anhydrous translucent sun blocker were prepared having the following formula:

| Mineral Oil | 10–17 |
| --- | --- |
| Purified Water - USP | 42.9–81 |
| Hydrogenated Castor oil | 3–8 |
| PEG-60 Lanolin | 1–5 |
| $C_{12-15}$ Alcohol benzoate | 1–5 |
| Silica | 1–8 |
| Mica | 0.5–5 |
| Titanium Dioxide | 0.5–4 |
| Octyl Methoxycinnamate | 1–7.5 |
| Benzophenone 3 | 1–5 |
| Dimethicone | 1–3 |

EXAMPLE 9

Using the procedure of Example 7, a sun blocker emulsion was prepared having the following formula:

| Purified Water - USP | 56–89.4 |
| --- | --- |
| Carbomer 934 | 0.1–0.5 |
| Benzophenone 3 | 1–5 |
| Octyl methoxycinnamate | 1–7.5 |
| Propyleneglycol | 1–4 |
| Polysorbate 80 | 1–3 |
| Stearic acid | 1–5 |
| Cetyl Palmitate | 1–2 |
| Glyceryl stearate | 1–2 |
| Cocoa butter | 1–2 |
| Phenyl dimethicone | 1–3 |
| Triethanolamine (85%) | 0.5–1 |
| Mica | 0.5–5 |
| Titanium Dioxide | 0.5–4 |

EXAMPLE 10

Using the procedure of Example 7, a sun blocker emulsion was prepared having the following formula:

| Purified Water - USP | 53–90.4 |
| --- | --- |
| Carbomer 934 | 0.1–0.5 |
| Benzophenone 3 | 1–5 |
| Octyl methoxycinnamate | 1–7.5 |
| Polysorbate 80 | 1–5 |
| Stearic acid | 1–5 |
| Cetyl Palmitate | 1–5 |
| Glyceryl stearate and PEG-60 stearate | 1–3 |
| Cetyl Alcohol | 1–5 |
| Cyclomethicone | 1–3 |
| Triethanolamine (85%) | 0.5–1 |
| Mica | 0.5–5 |
| Titanium Dioxide | 0.5–4 |

EXAMPLE 11

Using the procedure of Example 7, a sun blocker emulsion was prepared having the following formula:

| Mineral Oil | 24.4–86.85 |
| --- | --- |
| $C_{12-15}$ Alcohol benzoate | 5–20 |
| Isopropyl Palmitate | 1–20 |
| PEG-7 glyceryl cocoate | 1–5 |
| Cetearyl Isononanoate | 1–5 |
| Octyl Methoxycinnamate | 1–7.5 |
| Benzophenone-3 | 1–5 |
| Phenyl dimethicone | 1–3 |
| dl-alpha-tocopherol | .1–1 |
| Mica | 0.5–5 |
| Titanium Dioxide | 0.5–4 |
| Ironoxides | 0.05–0.10 |

EXAMPLE 12

Using the procedure of Example 7, a skin preparation having the following formula (weight percent) was prepared:

| Stearic Acid | 5.0 |
| --- | --- |
| Jojoba Oil | 4.0 |
| Propylene Glycol | 4.0 |
| Octylmethoxycinnamate | 5.0 |
| Benzophenone-3 | 4.0 |
| Mica (and) Titanium Dioxide | 4.0 |
| Bismuth Oxychloride | 2.0 |
| Triethanolamine (99%) | 2.5 |
| PEG-40 Stearate | 2.0 |
| Cetyl Alcohol | 2.0 |
| Tocopherol Acetate | 1.5 |
| Stearyl Alcohol | 1.0 |
| Methylparaben | 0.25 |
| Propylparaben | 0.15 |
| Allantoin | 0.1 |
| Deionized Water | q.s |

EXAMPLE 13

Using the procedure of Example 7, an ahydrous skin preparation was prepared having the following formula (in weight percent):

| | |
|---|---|
| C$_{10-30}$ carboxylic acid sterol ester | 10.0 |
| PPG-2 myristyl ether propionate | 10.0 |
| Emulsifying wax NF | 7.5 |
| Mineral Oil | 47.5 |
| Stearyl Heptanoate | 10.0 |
| TiO$_2$ | 2.0 |
| Mica | 2.0 |
| Benzophenone-3 | 3.5 |
| Octylmethoxycinnamate | 7.5 |

EXAMPLE 14

Using the procedure of Example 7, a an emulsion was prepared having the following formula (in weight percent):

| | |
|---|---|
| Mineral Oil | 42.0 |
| TiO$_2$ | 2.0 |
| Mica | 2.0 |
| Octylmethoxycinnamate | 7.0 |
| Benzophenone-3 | 4.0 |
| Microcrystalline wax | 7.5 |
| Paraphin wax | 7.5 |
| Polysorbate 80 (Tween ® '80) | 5.0 |
| Sorbitan oleate (Span ® 80) | 5.0 |
| Vitamin E | 0.1 |
| Purified Water USP | 17.9 |

EXAMPLE 15

Using the procedure of Example 7, a skin protective preparation was prepared having the formula (in weight percent):

| | |
|---|---|
| PEG-10 soya sterol | 1.0 |
| Octo dodecyl steroyl stearate | 3.0 |
| Glycerol stearate | 2.0 |
| Cetyl Alcohol | 3.0 |
| Dimethicon | 2.0 |
| Benzophenone-3 | 3.15 |
| Propylparaben | 0.1 |
| Mineral oil | 7.0 |
| BHA | 0.05 |
| Mica | 2.0 |
| Titanium Dioxide | 2.0 |
| Carbomer 934 | 0.4 |
| Methylparaben | 0.3 |
| Tetrasodium EDTA | 0.03 |
| Glycerine | 5.0 |
| Octylmethoxycinnamate | 7.35 |
| Triethanolamine (44%) | 1.65 |
| Imidazolidinyl urea | 0.25 |
| Water | q.s |

EXAMPLE 16

The sunscreen efficacy of the compositions embodying the present invention, measured with a Cary 14 Double Beam Spectrophotometer is in the full IR spectrum, that is, between 700 and 2600 nanometers. The meter was selected because it measures both incident and transmitted energy at any wave length while scanning the spectrum of wave lengths. A slit lamp is used to control the wave length of the transmitted radiation.

In conducting the measurements, a Xenon lamp was used as the IR source and a substrate formed of an IR transparent material such as MYLAR ®-D was interposed between the IR source and the meter. Each test composition is dispersed upon the substrate at a concentration of two microliters per square centimeter. The meter permitted a measurement of the percentage of the total infrared blocked by the substrate. The products produced according to Examples 12-15 and products produced in conformance to Examples 1-11 were measured by the Spectrophotometric method and in each case blocked 50% or more of the infrared radiation directed at the substrate.

EXAMPLE 17

The procedures of Example 16 were repeated using excised mouse skin (obtained from the Skin and Cancer Hospital, Philadelphia, PA) as the substrate instead of the MYLAR ®.

The substrate was coated first with a mineral oil base and then with a formulation containing 2 percent (by weight) of titanium dioxide and 2 percent coated mica in mineral oil (Analysis: 96% mineral oil; 2.77% TiO$_2$; and 1.23% mica). The results obtained, shown in Table A, below, are especially significant because they were obtained using a recognized laboratory equivalent to human skin.

TABLE A

| Formulation | % Through Mouse Epidermis |
|---|---|
| Mineral Oil Base | 100.0% |
| Base plus TiO$_2$ plus coated mica | 38.5%* |

*(Percent "blocked" equals 61.5%)

EXAMPLE 18

In order to evaluate the contributions of each component of the composition, each ingredient was separately formulated into a water/oil emulsion base and measured for adsorption. In addition, a formulation containing both chemical sunscreens, i.e., the UV absorbers, represented by benzophenone-3 and Parsol Hydro (diethanolamide methoxy cinnamate) was prepared and tested. The physical blockers of the present invention, i.e., titanium dioxide and coated mica (TIMIRON TM) were likewise combined in a single formulation and tested, which as shown in Table B, demonstrated unexpected synergism.

TABLE B

| Code | Component | Mean % Absorption |
|---|---|---|
| A | Emulsion base | 0 |
| B | Parsol Hydro* | 0 |
| C | Benzophenone-3* | 13.0 |
| D | Titanium dioxide* | 22.5 |
| E | Coated mica (TIMIRON TM)* | 14.3 |
| F | B + C* | 8.0 |
| G | D + E* | 42.8 |
| H | B + C + D + E | 53.0 |

Note:
*means in emulsion base A

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended here.

Accordingly, what is claimed is:

1. A method of protecting mammalian skin from the harmful effects of solar infrared radiation having a wave length of from 700-2600 nanometers comprising applying to skin in need thereof a preparation containing, in weight percent, from about 0.5 to about 4 percent titanium dioxide and from about 0.5 to about 5 percent mica, each dispersed in a nontoxic, non-irritating cosmetically acceptable carrier.

2. A method of protecting mammalian skin according to claim 1 in which said carrier is an emulsion.

3. A method of protecting mammalian skin according to claim 1 in which said carrier is an anhydrous solvent.

4. A method of protecting mammalian skin according to claim 1 in which said carrier is a mineral oil.

* * * * *